United States Patent [19]

Dennis et al.

[11] Patent Number: 4,567,306

[45] Date of Patent: Jan. 28, 1986

[54] CONTINUOUS PROCESS FOR THE PRODUCTION OF ALDEHYDES BY HYDROFORMYLATION OF OLEFINS

[75] Inventors: Alan J. Dennis, Middlesbrough; George E. Harrison, Billericay; James P. Wyber, Stockton-on-Tees, all of England

[73] Assignee: Davy Mckee (London) Limited, London, England

[21] Appl. No.: 680,834

[22] Filed: Dec. 12, 1984

[30] Foreign Application Priority Data

Dec. 23, 1983 [GB] United Kingdom ............... 8334359

[51] Int. Cl.⁴ .............................................. C07C 45/50
[52] U.S. Cl. .................................. 568/455; 568/454; 502/155
[58] Field of Search ............... 568/454, 455; 502/155; 260/429 R

[56] References Cited

U.S. PATENT DOCUMENTS

| | | | |
|---|---|---|---|
| 3,725,483 | 4/1973 | Deffner et al. | 568/455 |
| 3,733,361 | 5/1973 | Deffner et al. | 568/455 |
| 3,857,895 | 12/1974 | Booth | 568/455 |
| 4,179,403 | 12/1979 | Kim | 568/455 |
| 4,496,768 | 7/1985 | Dennis et al. | 568/454 |
| 4,496,769 | 7/1985 | Dennis et al. | 568/454 |

Primary Examiner—Werren B. Lone
Attorney, Agent, or Firm—Bernard, Rothwell & Brown

[57] ABSTRACT

A continuous hydroformylation process for the production of an aldehyde by hydroformylation of an olefin comprises:

providing a hydroformylation zone containing a charge of a liquid reaction medium having dissolved therein (a) a complex rhodium hydroformylation catalyst comprising rhodium in complex combination with carbon monoxide and with a cyclic phosphite having a phosphorus atom linked to three oxygen atoms at least two of which form together with the phosphorus atom part of a ring and (b) a ligand stabilizing amount of a tertiary amine;

supplying said olefin to the hydroformylation zone;

maintaining temperature and pressure conditions in the hydroformylation zone conducive to hydroformylation of the olefin;

supplying make-up hydrogen and carbon monoxide to the hydroformylation zone; and recovering from the liquid hydroformylation medium a hydroformylation product comprising at least one aldehyde.

17 Claims, No Drawings

CONTINUOUS PROCESS FOR THE PRODUCTION OF ALDEHYDES BY HYDROFORMYLATION OF OLEFINS

This invention relates to a hydroformylation process.

Hydroformylation is a well known reaction in which an olefin (usually a terminal olefin) is reacted under suitable temperature and pressure conditions with hydrogen and carbon monoxide in the presence of a hydroformylation catalyst to give an aldehyde, or a mixture of aldehydes, having one more carbon atom than the starting olefin. Thus ethylene yields propionaldehyde, whilst propylene yield a mixture of n- and iso-butyraldehydes, of which the straight chain n-isomer is usually the more commercially desirable material. In some cases the catalyst and/or the process conditions can be modified so that the products are not aldehydes but are the corresponding alcohols.

The catalysts first used in this reaction were cobalt-containing catalysts, such as cobalt octacarbonyl. It is widely accepted that the cobalt octacarbonyl is converted to hydrido cobalt tetracarbonyl under the reaction conditions and that this compound constitutes the active catalyst species. The use of such catalysts necessitates exceptionally high operating pressures, e.g. several hundred bars, in order to maintain the catalysts in their active form. The n-/iso-molar ratio of the aldehyde products is not particularly high, e.g. about 3:1 or 4:1, and product recovery is generally complicated because the cobalt carbonyl catalysts are volatile and chemically unstable in the absence of high hydrogen and carbon monoxide partial pressures.

More recently there have been proposed rhodium complex hydroformylation catalysts for hydroformylation of alpha-olefins, that is to say compounds containing the group $-CH=CH_2$ or $>C=CH_2$. These catalysts generally comprise rhodium in complex combination with carbon monoxide and with a ligand, such as triphenylphosphine and are used in conjunction with excess ligand. Such rhodium complex catalysts are now in use in numerous hydroformylation plants throughout the world and many plants formerly operating with cobalt catalysts have been, or are being, converted for operation with these newer rhodium catalysts. Such catalysts have the advantage not only of lower operating pressures e.g. about 20 kg/cm$^2$ absolute (19.6 bar) or less, but also of being capable of yielding high n-/iso-aldehyde product ratios from alpha-olefins; in many cases n-/iso-aldehyde molar ratios of 10:1 and higher can be achieved. Moreover, since the catalyst is nonvolatile, product recovery is greatly simplified. A fuller description of the process will be found in the article "Low-pressure OXO process yields a better product mix", Chemical Engineering, Dec. 5, 1977, pages 110 to 115. Also extremely relevant to this process are U.S. Pat. No. 3,527,809 and British Patent Specifications Nos. 1,338,237 and 1,582,010.

The rhodium catalyst adopted in commercial practice comprises rhodium in complex combination with carbon monoxide and with triphenylphosphine. Although the nature of the catalytic species is not entirely clear, it has been postulated to be $HRh(CO)(PPh_3)_3$ (see, for example, page 792 of "Advanced Inorganic Chemistry" (Third Edition) by F. Albert Cotton and Geoffrey Wilkinson, published by Interscience Publishers). The reaction solution contains excess triphenylphosphine and operating temperatures in the range of from about 90° C. to about 120° C. are recommended.

The process of U.S. Pat. No. 3,527,809, which is the process used commercially, is restricted to use of alpha-olefinic compounds such as ethylene, propylene, butene-1, and hexene-1, i.e. compounds with a terminal $-CH=CH_2$ or $>C=CH_2$ group. Although terminal olefins can be successfully hydroformylated in high yield to the corresponding straight chain aldehydes (e.g. propylene can be hydroformylated to n-butyraldehyde) using this process, we have found that the use of non-terminal olefins, such as butene-2, with a view to producing the iso-aldehyde (e.g. 2-methylbutyraldehyde from butene-2) is much less successful than with terminal olefins, such as butene-1, because such internal olefins are much less reactive than the corresponding terminal olefins, and higher operating temperatures are hence required in order to achieve acceptable reaction rates and product aldehyde yields. However, the use of higher operating temperatures is accompanied by an increasing tendency for the internal olefin to undergo isomerisation, with a consequent reduction in the yield of the desired iso-aldehyde. Hence butene-2 tends to undergo isomerisation to butene-1 under the harsher conditions required for hydroformylation of butene-2 so that a proportion of the butene-2 is converted to n-valeraldehyde rather than to the desired iso-butyraldehyde. In addition, the catalyst appears to be less stable at the increased operating temperatures required for adequate reaction rates so that the rate of deactivation of the catalyst becomes undesirably high. For these reasons we consider that rhodium complex catalysts using triphenylphosphine as ligand are not commercially acceptable for hydroformylation of internal olefins.

U.S. Pat. No. 3,527,809 also proposes the use of various other ligands, including phosphites, such as triphenylphosphite, in place of triphenylphosphine. Although the use of triphenylphosphite has the advantage that lower operating temperatures can be used in the hydroformylation of internal olefins, we have found that the catalyst tends to deactivate moderately rapidly, a phenomenon that is accompanied by disappearance of free triphenylphosphite ligand and by an increase in the rate of formation of "heavy" materials (i.e. high boiling byproducts). Further teaching as to the use of phosphites in hydroformylation of terminal olefins will be found in U.S. Pat. Nos. 3,917,661, 3,499,933 and 4,262,142. There are numerous other references in the literature to the use of phosphite ligands in homogeneous rhodium complex hydroformylation catalysts. Examples include U.S. Pat. Nos. 3,547,964, 3,560,539, 3,641,076, 3,644,446, 3,859,359, 3,907,847, 3,933,919, 3,956,177, 4,096,192, 4,101,588, 4,108,905, 4,135,911, 4,158,020, 4,195,042, 4,224,255 and 4,267,383, as well as British Patent Specifications Nos. 995,459, 1,207,561, 1,228,201, 1,243,189, 1,243,190, 1,263,720, 1,338,225, 1,448,090, 1,455,645, 1,460,870, 1,461,900, 1,462,342, 1,463,947, 1,557,396, and 1,586,805, European Patent Publications Nos. 0003753 and 0028892, and International Patent Publication No. WO 80/00081. Other examples include Japanese Patent Publications Nos. 10765/69 published May 19, 1969 and 40326/73 published Nov. 30, 1973.

Example 2 of British Patent Specification No. 1,325,199 teaches the use, in a batch reaction for the hydroformylation of hexene-1, of the catalyst ]RhCl(CO)(tmpP)$_2$] where tmp represents the radical

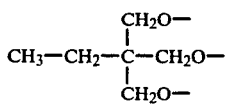

Reaction is effected in the liquid phase using a 50% v/v solution of hexene-1 in benzene. At 100° C. 57 mol% conversion of hexene-1 is said to be achieved in 6 hours under partial pressures of carbon monoxide and hydrogen of 12 atmospheres (about 12 bar) to give a reported yield of aldehydes (based on hexene-1 converted) of 100%, of which 65 mol% is 1-heptanal. According to page 2, lines 55 to 61, catalysts devoid of chlorine are as efficient as those containing it, whilst the process is said to be capable of use with alpha-olefins as well as nonterminal olefins, e.g butene-2, pentene-2, and hexene-2 (page 2, lines 93 to 101). According to page 5, lines 7 to 12, when using similar catalysts with hexene-2 at 100° C., 35 to 38% of the aldehydes formed is 1-heptanal. Conversions of only 57% in 6 hours are not commercially interesting, nor are terminal aldehydes necessarily the most desirable products obtained by hydroformylating internal olefins.

The reaction of 4-ethyl-2,6,7-trioxa-1-phosphabicyclo-[2,2,2]-octane with dodecacarbonyltetrarhodium of the formula $Rh_4(CO)_{12}$ to form compounds of the formulae $Rh_4(CO)_{10}L_2$, $Rh_4(CO)_9L_3$ and $Rh_4(CO)_8L_4$, where L is the compound $P(OCH_2)_3CEt$, is described by B. L. Booth et al in J. Organometal. Chem. 27 (1971) 119–131. These authors also describe production of complexes of the type $Rh_6(CO)_{10}L_6$, in which L is as defined above, when the same organophosphorus compound is reacted under similar conditions with hexadecacarbonylhexarhodium of the formula $Rh_6(CO)_{16}$. They also describe experiments, summarised in Tables 2 and 3 on page 123 of this article, in which various alkenes were hydroformylated in the presence of $Rh_4(CO)_{12}$ or $Rh_6(CO)_{16}$ and of ETPO, which is identified in a footnote on page 119 as 4-ethyl-2,6,7-trioxa-1-phosphabicyclo-[2,2,2]-octane. Further experimental details are given on pages 129 and 130. These experiments were all batch experiments carried out at 120 bar and used a phosphorus ligand:Rh molar ratio of 1:1, as well as a $CO:H_2$ molar ratio of 1:1 in all cases. Reaction times of 3 hours for 0.20 mmole of olefin were used in all experiments reported.

The use of tertiary amines in hydroformylation media has been suggested previously in a number of publications. For example, British Patent Specifications Nos. 1198815 and 1198816 and U.S. Pat. Nos. 3,560,572, 3,624,158, 3,644,529 and 3,725,483 describe the use of tertiary amines to increase the thermal stability of cobalt containing complex hydroformylation catalysts during product recovery.

Tertiary amines, such as pyridine and triphenylamine, have also been suggested as the ligand for rhodium-containing hydroformylation catalysts as an alternative to the tertiary phosphine or phosphite normally used. Examples of such teachings are to be found in British Patent Specifications Nos. 1138601, 1173568, 1207561, 1228201, 1243189 and 1243190.

U.S. Pat. No. 3,857,895 teaches use of phosphine ligands containing an amino or amidino group in rhodium complex hydroformylation catalysts. If desired a polycyclic amine such as triethylene diamine (i.e. 1,4-diazabicyclo-[2,2,2]-octane) can be included in the reaction medium.

It has also been proposed to use an amine, such as pyridine, as a solvent in a rhodium catalysed hydroformylation process. In this connection the reader's attention is directed to British Patent Specifications Nos. 1138237 and 2072168A.

British Patent Specification No. 1263720 proposes use as a hydroformylation catalyst of a complex of a Group VIII metal other than iron, nickel, palladium and platinum (for example, rhodium) which contains at least one metal complexing ligand containing an atom of a Group Vb or VIb element having a single pair of electrons available for donation (e.g. pyridine) and a bidentate ligand co-ordinating through oxygen and nitrogen and selected from a quinaldinate, 8-oxyquinolinate and a salicylaldoximate.

U.S. Pat. Nos. 3,547,964, 3,560,539 and 3,641,076 teach a process for recovery of catalyst from a hydroformylation reaction medium containing a Group VIII metal (e.g. rhodium) halide or hydride complex with carbon monoxide and a biphyllic ligand (such as triphenylphosphine), which medium may also contain as cocatalyst a polycyclic, heterocyclic, saturated amine having at least one nitrogen in a bridgehead position, for example 1,4-diazabicyclo-[2,2,2]-octane (otherwise known as triethylene diamine). In each of U.S. Pat. Nos. 3,547,964 and 3,641,076 it is mentioned that, instead of triphenylphosphine, the biphyllic ligand can alternatively be a phosphite, such as triphenylphosphite or tricyclohexylphosphite. Further description of such media can be found in U.S. Pat. No. 4,267,383. In none of these specifications, however, is there any specific example in which the medium contains a phosphite ligand.

Rhodium complex hydroformylation catalysts which incorporate a bidentate ligand, such as 1,1'-bis-(diphenylphosphino)-ferrocene, as well as a monodentate ligand, such as tri-iso-butylamine or triphenylamine are described in U.S. Pat. No. 4,169,861. Similar rhodium complexes are described in U.S. Pat. No. 4,201,728.

Rhodium complex hydroformylation catalysts that contain halogen or pseudo-halogen in addition to a ligand, such as triphenylphosphine or triphenylphosphite, have been proposed for use, but it has been recognised that an inhibition period is observed with such catalysts. However, according to British Patent Specification No. 1338225 and U.S. Pat. Nos. 4,200,591 and 4,200,592, addition of an organic base, such as $Et_3N$, causes this inhibition period to disappear. The function of the base is to act as a hydrogen halide or pseudo-halide acceptor. The base plays no further part in the hydroformylation process once this function has been discharged. British Patent Specification No. 2000124A also discloses addition of an organic base, such as $Et_3N$, as an acceptor for hydrogen halide or pseudo-halide when a hydrido carbonyl complex of rhodium is generated in situ from a corresponding halogen or pseudo-halogen containing complex. In acting as acceptor the amine presumably reacts to give a non-volatile hydrohalide or -pseudohalide salt, whilst any free remaining triethylamine will quickly be lost from the reaction solution during distillation for aldehyde recovery if the process is operated continuously.

A further report of the removal of the induction period for a hydroformylation reaction upon addition of triethylamine has appeared in a paper by D. Evans et al, J. Chem. Soc., (A), 1968, 3133.

According to Japanese Patent No. 647225 (1972), amines and KOH have proved to be effective as dehalogenation agents.

In a paper in Bulletin of The Japan Petroleum Institute, Volume 19, No. 1, May 1977, pages 62 to 67, Yasuchi Matsui et al reported the effect of dehalogenation agents on hydroformylation reactions catalysed by rhodium complexes. In Table 3 on page 65 of this paper they indicate that a catalyst life in excess of 10 hours can be attained by adding tri-n-octylamine, a mixture of triethanolamine and KOH, or tri-n-butylamine to a catalyst system including triphenylphosphite and the complex, $RhH(CO)(PPh_3)_3$. They state:

"Therefore, these bases seem not only to be the dehalogenation agents but also stabilizers of the catalyst. It is speculated that these bases prevent the degradation products of ligand from forming coordinate complexes with rhodium."

British Patent Specification No. 1448090 describes for use as hydroformylation catalysts certain ionic rhodium complexes containing, in addition to carbon monoxide, a ligand which can be a tertiary organonitrogen compound such as triphenylamine, as well as a non-coordinating anionic moiety.

The addition of acids to hydroformylation media has been advocated in U.S. Pat. No. 4,224,255 and in International Patent Publication No. WO 80/00081. The catalysts for use in such processes can contain triarylphosphite ligands, it is said. The addition of acids, such as o-phthalic acid, is said to suppress hydrogenation reactions.

It is also been proposed to add water to a hydroformylation reaction medium. Thus U.S. Pat. No. 4,258,215 teaches use of a two-phase system, one phase of which is aqueous, in the hydroformylation of $C_2$ to $C_{20}$ alpha-olefins using a complex catalyst consisting essentially of rhodium in combination with carbon monoxide and a triorganophosphorus ligand, such as a triarylphosphite. It is said to be quite unexpected that the introduction of water would produce an enhancement in the reaction rate.

Addition of water and an alkali metal hydroxide or ammonium hydroxide to a hydroformylation reaction medium is taught by U.S. Pat. No. 3,511,880.

In our co-pending patent application Ser. No. 501,920, filed June 7, 1983 (now U.S. Pat. No. 4,496,769) we have shown that, in a continuous hydroformylation process in which there is used as ligand in a rhodium complex catalyst an "open" phosphite, such as triphenylphosphite, in which the phosphorus atom does not form part of a ring, the ligand decays in the course of time, probably through formation of 1:1, 2:1, and 3:1 aldehyde:phosphite adducts and the like as described by F. Ramirez, Pure & Applied Chemistry (1964), Vol 9, pages 337 to 369, at page 356 et seq. Hence, we proposed in this specification that, in order to maintain catalytic activity, further phosphite ligand is added to replace that which has decayed.

In our co-pending patent application Ser. No. 501,859, filed June 7, 1983 (now U.S. Pat. No. 4,496,768) we have described a continuous process for the hydroformylation of alpha-olefins using a catalyst comprising rhodium in complex combination with a cyclic phosphite having a bridgehead phosphorus atom linked to three oxygen atoms at least two of which form together with the bridgehead phosphorus atom part of a ring. Typical of such cyclic phosphites are the derivatives of 2,6,7-trioxa-phosphabicyclo-[2,2,2]-octane, of which 4-ethyl-2,6,7-trioxa-1-phosphabicyclo-[2,2,2]-octane is an example. A similar continuous process for the hydroformylation of internal olefins is described in our co-pending patent application Ser. No. 501,928, filed June 7, 1983 (now U.S. Pat. No. 4,482,749).

In the course of investigating the processes of these last two mentioned co-pending patent applications we have discovered that, although they can be successfully operated on a continuous basis for extended periods of time, a certain slow degradation of catalyst activity is observed, particularly when working with alpha-olefins or when working at temperatures towards or above the upper end of the recommended range. This loss of catalyst activity appears to be associated with loss of phosphite ligand. Although some compensation for this slow deactivation can be made by addition from time to time of further quantities of ligand, it would be desirable to provide a method of maintaining catalyst activity and-/or minimising loss of cyclic phosphite ligand.

It is accordingly an object of the present invention to provide a method of improving the stability of rhodium hydroformylation catalysts that utilise cyclic phosphite ligands.

According to the present invention there is provided a continuous hydroformylation process for the production of an aldehyde by hydroformylation of an olefin which comprises:

providing a hydroformylation zone containing a charge of a liquid reaction medium having dissolved therein (a) a complex rhodium hydroformylation catalyst comprising rhodium in complex combination with carbon monoxide and with a cyclic phosphite ligand having a phosphorus atom linked to three oxygen atoms at least two of which form together with the phosphorus atom part of a ring and (b) a ligand stabilising amount of a tertiary amine;

supplying said olefin to the hydroformylation zone;

maintaining temperature and pressure conditions in the hydroformylation zone conducive to hydroformylation of the olefin;

supplying make-up hydrogen and carbon monoxide to the hydroformylation zone; and recovering from the liquid hydroformylation medium a hydroformylation product comprising at least one aldehyde.

In our process the function of the tertiary amine is primarily to stabilise the cyclic phosphite ligand and to prevent its decay or decomposition under the reaction conditions employed. Moreover, it appears from our experiments that the cyclic phosphite ligands used in our process are unique amongst phosphite ligands in this respect. Thus, when additions of a tertiary amine are made to hydroformylation reaction media containing an "open" phosphite ligand, such as triphenyl phosphite, the decay of the "open" phosphite ligand under hydroformylation conditions, which we noted in our co-pending patent application Ser. No. 501,920 filed June 7, 1983 (now U.S. Pat. No. 4,496,769), is not halted. Hence our investigations suggest that tertiary amines do not stabilise "open" phosphites, such as triphenyl phosphite. This means that, although a tertiary amine may help to preserve the stability of a rhodium hydroformylation catalyst in the initial stages of operation, as observed by Yasuchi Matsui et al, loc. cit., it cannot stabilise for more than a few hours a rhodium complex hydroformylation catalyst that utilises an "open" phosphite ligand because the phosphite ligand decays, despite the presence of the tertiary amine, until no free ligand is left to maintain catalyst activity and stability.

The catalyst used in the process of the present invention is a rhodium carbonyl complex comprising rhodium in complex combination with carbon monoxide and with a cyclic organic phosphite ligand having a phosphorus atom linked to three oxygen atoms at least two of which form, together with the phosphorus atom to which they are attached, part of a ring. Preferably this catalyst and the reaction medium are substantially halogen-free. Although the structure of such rhodium carbonyl complexes is not entirely clear, it is postulated that the preferred halogen-free complexes may have the structure:

$$RhH_m(CO)_n(L)_p$$

in which m is zero, 1 or 2, n and p are each, independently of the other, an integer of from 1 to about 4, and L is a cyclic phosphite ligand as defined above, provided that the sum of m, n and p is from 4 to 6.

The olefin may be an optionally substituted alpha-olefin which contains at least one alpha-olefinic carbon-carbon double bond (or ethylenic bond) and which contains at least 2 carbon atoms. Such compounds have the general formula:

$$R_1R_2C=CH_2$$

in which $R_1$ and $R_2$ each independently represent a hydrogen atom or an organic radical or together represent a divalent radical which, together with the carbon atom to which thye are attached, form a carbocyclic or heterocyclic ring. (For convenience hereafter the term "alpha-olefin" is some times used to designate "optionally substituted alpha-olefin"). Preferably such alpha-olefins are halogen-free and sulphur-free. Preferably the olefinically unsaturated compound contains from 2 to about 20 carbon atoms. Illustrative starting olefins include alpha-olefins, e.g. alkenes, arylalkenes, and cycloalkenes, and substituted alpha-olefins, e.g. ethers of unsaturated alcohols, and esters of unsaturated alcohols and/or acids.

As examples of alpha-olefins there may be mentioned 1-alkenes (e.g. ethylene, propylene, butene-1, iso-butylene, pentene-1, 2-methylbutene-1, hexene-1, heptene-1, ocetene-1, 2,4,4-trimethylpentene-1, nonene-1, 2-propylhexene-1, decene-1, undecene-1, dodecene-1, octadecene-1, eicosene-1, 3-methylbutene-1, 3-methylpentene-1, 3-ethyl-4-methylphentene-1, 3-ethylhexene-1, 4,4-dimethylnonene-1, 6-propyldecene-1, 1,5-hexadiene, vinyl cyclohexane, allyl cyclohexane, styrene, alpha-methylstyrene, allylbenzene, divinylbenzene, 1,1-diphenylethylene, o-vinyl-p-xylene, p-vinylcumene, m-hexylstyrene, 1-allyl-4-vinylbenzene, beta-vinylnaphthalene, and the like), alpha-alkenols (e.g. allyl alcohol, hex-1-en-4-ol, oct-1-en-4-ol, and the like), alpha-alkenyl ethers (e.g. vinyl methyl ether, vinyl ethyl ether, allyl ethyl ether, allyl t-butyl ether, allyl phenyl ether, and the like), alpha-alkenyl alkanoates (e.g. vinyl acetate, allyl acetate, and the like), alkyl alpha-alkenoates (e.g. methyl acrylate, ethyl acrylate, n-propyl oct-7-enoate, methyl methacrylate, and the like), alpha-olefinically unsaturated aldehydes and acetals (e.g. acrolein, acrolein dimethyl and diethyl acetals, and the like), alpha-olefinically unsaturated nitriles (e.g. acrylonitrile and the like), and alpha-olefinically unsaturated ketones (e.g. vinyl ethyl ketone, and the like).

The olefin may alternatively be an optionally substituted internal olefin contains at least one internal olefinic carbon-carbon double bond (or ethylenic bond) and contains at least 4 carbon atoms. Such compounds have the general formula:

$$R_3R_4C=CR_5R_6$$

in which $R_3$ and $R_5$ each independently represent a hydrogen atom or an organic radical or together represent a divalent radical which, together with the indicated carbon atoms, form a carbocyclic or heterocyclic ring, and $R_4$ and $R_6$ each independently represent an organic radical or together represent a divalent radical which, together with the indicated carbon atoms, form a carbocyclic or heterocyclic ring. (For convenience hereafter the term "internal olefin" is some times used to designate "optionally substituted internal olefin"). Preferably such internal olefins are halogen-free and sulphur free. Preferably the internal olefin contains from 4 to about 20 carbon atoms. It is especially preferred that the internal olefin shall contain at least one hydrogen atom adjacent to the olefinic double bond, that is to say that the internal olefin is of the formula $R_2C=CHR$ or of the formula $RHC=CHR$, where each R, independently of the others, represents an organic radical.

Illustrative starting olefins include internal olefins, e.g. alkenes, arylalkenes, and cycloalkenes, and substituted internal olefins, e.g. ethers of unsaturated alcohols, and esters of unsaturated alcohols and/or acids.

As examples of internal olefins there may be mentioned cis- and trans-butene-2, 2-methylbutene-2, 2,3-dimethylbutene-2, 1,2-diphenylethylene, hexene-2, hexene-3, cis- and trans-heptene-2, octene-2, octene-3, ocetene-4, 3-methylheptene-2, 3-methylheptene-3, 3-methylheptene-5, 3,4-dimethyl-hexene-2, decene-2, tetradecene-2, 4-amyldecene-2, 4-methyltridecene-2, octadecene-2, 6,6-dipropyldecene-3, prop-1-enylbenzene, 3-benzylheptene-3, cyclobutene, cyclopentene, cyclohexene, cycloheptene, cyclooctene, 1-methylcyclohexene, diethyl maleate, diethyl fumarate, crotonaldehyde, crotonaldehyde dimethyl acetal, ethyl cinnamate, cis- and trans-prop-1-enyl t-butyl ether, and the like, as well as a mixture of two or more thereof.

The olefin may be supplied to the hydroformylation zone in substantially pure form. Alternatively it may be admixed with one or more other olefins and/or inert materials such as saturated hydrocarbons. Besides the olefin(s), hydrogen and carbon monoxide, there may be supplied to the hydroformylation zone one or more inert materials, such as inert gases (e.g. nitrogen, argon, carbon dioxide and gaseous hydrocarbons, such as methane, ethane, and propane). Such inert gases may be present in the olefin feedstock or in the synthesis gas. Other inert materials may include hydrogenation by-products of the hydroformylation reaction, e.g. n-butane where the olefin is butene-1 or butene-2.

In many cases the process may be operated so that a part only of the make-up olefin, e.g. from about 15% to about 80% or higher, is converted in passage through the hydroformylation zone. Although the process can be operated on a "once through" basis, with unreacted olefin being exported beyond battery limits, possibly for other uses, after product recovery, it will usually be desirable to recycle unreacted olefin, after product recovery, to the hydroformylation zone. As some isomerisation of olefin may occur in passage through the hydroformylation zone (e.g. in the case of butene-2 some isomerisation to butene-1 may occur), the recycle olefin stream may contain isomerised olefin, even though the olefin feedstock is substantially pure. In addition it may contain byproduct hydrogenated feedstock. The concentration of isomerised olefin and of inert materials in the recycle stream or streams can be controlled in the usual way by taking purge streams at appropriate controlled rates.

The organic phosphite ligand is preferably an at least bicyclic compound which contains a phosphorus atom in a bridgehead position linked to three oxygen atoms, each forming part of a cyclic system. Such ligands can be represented by the general formula:

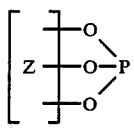  (I)

in which Z represents a trivalent organic group. In formula (I) Z may be acyclic or may comprise a cyclic group; in the former case the ligand of formula (I) is a bicyclic organic phosphite, whilst in the latter case the ligand of formula (I) is a tri- or poly-cyclic organic phosphite. As an example of a ligand of formula (I) in which Z comprises a cyclic group there can be mentioned the compound 2,8,9-trioxa-1-phosphatricyclo-[3.3.1.1$^{3,7}$]-decane of the formula:

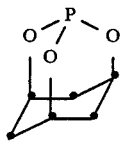  (II)

Other preferred organic bicyclic phosphite ligands are those of the general formula:

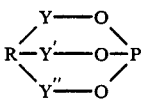  (III)

in which Y, Y' and Y" each, independently of the others, represent a divalent organic radical, and R is a trivalent atom or group. Such compounds can be prepared by the methods described in the literature, for example, by transesterification of an organic phosphite of the general formula:

(R'O)$_3$P  (IV), in which each R' is an optionally substituted hydrocarbon radical, for example an optionally substituted alkyl or aryl radical, such as methyl, ethyl, phenyl, benzyl, o-tolyl, naphthyl, hydroxymethyl or hydroxyethyl, with a triol or higher polyol of the general formula:

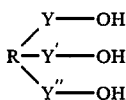  (V)

in which R, Y, Y' and Y" are as defined above. One method of effecting transesterification comprises boiling the phosphite of formula (IV), e.g. triethyl phosphite, under reflux with a triol (or higher polyol) of formula (V), such as trimethylolpropane, optionally in the presence of a transesterification catalyst, e.g. sodium methoxide or triethylamine, and distilling off the alcohol of formula R'OH, e.g. ethanol, as it is formed.

Alternatively the cyclic organic phosphite ligand may be a monocyclic phosphite of the general formula:

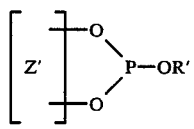  (VI)

in which Z' represents a divalent organic radical, which may be a cyclic or acyclic radical, and R' is as defined above. Preferred monocyclic ligands are those of the general formula:

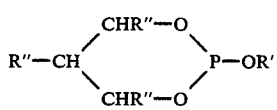  (VII)

in which R" represents a hydrogen atom or one of the meanings of R' (defined above). The compounds of general formula (VI) can be made by methods known in the art for example by transesterification of an organic phosphite of formula (IV) with a diol of formula:

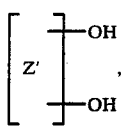  (VIII)

in which Z' is as defined above.

In such a transesterification reaction the phosphite of formula (IV), e.g. trimethyl phosphite, triethyl phosphite, or triphenyl phosphite, may be heated under reflux with the diol of formula (VIII), optionally in the presence of a transesterification catalyst. Typical diols of formula (VIII) include 1,3-diols such as propane-1,3-diol and 2,2-dimethylpropane-1,3-diol, and hydrogenation products of alcohols and aldehyde condensation products such as "dimer (V)" of British Patent Specification No. 1338237.

As an example of a ligand of formula (VI) there can be mentioned 1-phenoxy-4,4-dimethyl-2,6-dioxa-1-phospha-cyclohexane (2,2-dimethyl-propane-1,3-diol phenyl phosphite).

Particularly preferred cyclic phosphite ligands are those in which the phosphorus atom forms part of one or more 6-membered rings.

In one preferred mode of operation the cyclic phosphite ligand is introduced as such into the hydroformylation reaction medium. Alternatively the ligand can be formed in situ by charging to the hydroformylation reaction medium a phosphite of a monohydric alcohol or phenol, e.g. trimethyl phosphite, triethyl phosphite, triphenyl phosphite, trinaphthyl phosphite, tri-n-butyl phosphite, tri-n-hexyl phosphite, or the like, and an at least equimolar quantity of an appropriate diol or of a polyol containing three or more hydroxyl groups, such as trimethylol propane or 1,3,5-trihydroxycyclohexane. Transesterification of the phosphite ester with the diol or polyol can be effected by heating the reaction medium, either before or after addition of the rhodium catalyst precursor, and either before or after commencement of hydroformylation.

In formula (III) R may represent, for example

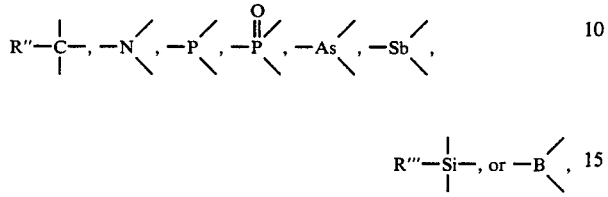

in which R" is as defined above, and R''' is alkyl or alkoxy, e.g. methyl or methoxy. As examples of divalent organic radicals for which Y, Y' and Y" may stand there may be mentioned alkylene, oxy-alkylene, alkylene-oxyalkylene, alkylene-NR''''-alkylene, arylene, oxyarylene, alkylene-arylene, arylene-alkylene, alkyleneoxy-arylene, and arylene-oxyalkylene; in such groups alkylene may be, for example, methylene, ethylene or ethylidene and arylene may be, for example, o-phenylene or m-phenylene, whilst R'''' represents an optionally substituted hydrocarbon radical, such as an alkyl radical. Preferably Y, Y' and Y" contain no more than about 20 atoms in the chain.

Particularly preferred ligands are those of formula (III) in which Y, Y' and Y" are methylene groups or substituted methylene groups, such as ethylidene groups. As examples of ligands of formula (III) there can be mentioned:

2,6,7-trioxa-1-phosphabicyclo-[2,2,2]-octane;
4-methyl-2,6,7-trioxa-1-phosphabicyclo-[2,2,2]-octane;
4-ethyl-2,6,7-trioxa-1-phosphabicyclo-[2,2,2]-octane;
4-hydroxymethyl-2,6,7-trioxa-1-phosphabicyclo-[2,2,2]-octane;
4-ethoxymethyl-2,6,7-trioxa-1-phosphabicyclo-[2,2,2]-octane;
4-acetoxymethyl-2,6,7-trioxa-1-phosphabicyclo-[2,2,2]-octane;
2,6,7-trioxa-1,4-diphosphabicyclo-[2,2,2]-octane;
4-iso-propyl-2,6,7-trioxa-1-phosphabicyclo-[2,2,2]-octane;
4-iso-propyl-3-methyl-2,6,7-trioxa-1-phosphabicyclo-[2,2,2]-octane;
4-n-butyl-2,6,7-trioxa-1-phosphabicyclo-[2,2,2]-octane;
4-n-hexyl-2,6,7-trioxa-1-phosphabicyclo-[2,2,2]-octane;
4-(2-ethylhexyl)-2,6,7-trioxa-1-phosphabicyclo-[2,2,2]-octane;
4-n-decyl-2,6,7-trioxa-1-phosphabicyclo-[2,2,2]-octane;
4-n-undecyl-2,6,7-trioxa-1-phosphabicyclo-[2,2,2]-octane;
3,5,8-trimethyl-2,6,7-trioxa-1-phosphabicyclo-[2,2,2]-octane;
3,4,5,8-tetramethyl-2,6,7-trioxa-1-phosphabicyclo-[2,2,2]-octane;
4-phenyl-2,6,7-trioxa-1-phosphabicyclo-[2,2,2]-octane;
4-cyclohexyl-2,6,7-trioxa-1-phosphabicyclo-[2,2,2]-octane;
4-capryloyloxymethyl-2,6,7-trioxa-1-phosphabicyclo-[2,2,2]-octane;
4-stearoyloxymethyl-2,6,7-trioxa-1-phosphabicyclo[2,2,2]-octane;
3,5,8-trimethyl-4-phenyl-2,6,7-trioxa-1-phosphabicyclo-[2,2,2]-octane;
4-benzyl-2,6,7-trioxa-1-phosphabicyclo-[2,2,2]-octane;
3,4-dimethyl-2,6,7-trioxa-1-phosphabicyclo-[2,2,2]-octane; and the like.

The reaction medium contains a stabilising amount of a tertiary amine. As examples of tertiary amines there can be mentioned in particular trialkylamines, such as triethylamine, tri-n-propylamine, tri-n-butylamine, tri-iso-butylamine, tri-iso-propylamine, tri-n-hexylamine, tri-n-octylamine, dimethyl-iso-propylamine, dimethylhexadecylamine, methyl-di-n-octylamine, and the like, as well as substituted derivatives thereof containing one or more noninterfering substituents such as hydroxy groups, for example triethanolamine, N-methyl-diethanolamine, tris-(3-hydroxypropyl)-amine, and the like. Heterocyclic tertiary amines can also be contemplated for use in the present invention, such as pyridine, 2-, 3- and 4-picoline, the lutidines, the collidines, N-methylpiperidine, N-methylmorpholine, N-2'-hydroxyethylmorpholine, quinoline, iso-quinoline, quinoxaline, acridine, quinuclidine and the like. Also suitable for use in the process of the present invention are aromatic tertiary amines, such as N,N-dimethylaniline, N,N-diethylaniline, N,N-dimethyl-p-toluidine, N-methyldiphenylamine, N,N-dimethylbenzylamine, N,N-dimethyl-1-naphthylamine, and the like. Compounds containing two or more tertiary amino groups, such as N,N,N',N'-tetramethylethylene diamine and triethylene diamine (i.e. 1,4-diazabicyclo-[2,2,2]-octane) can also be mentioned.

The rhodium complex catalyst is dissolved in a liquid reaction medium in the process of the invention. This reaction medium comprises in addition to the catalytic species and in addition to a stabilising amount of a tertiary amine, product aldehyde(s), aldehyde condensation products, olefin, hydrogenation product(s) derived from the olefin, and preferably also excess cyclic phosphite ligand. The nature of the aldehyde condensation products, and possible mechanisms for their formation during the course of the hydroformylation reaction, is explained in more detail in British Patent Specification No. 1,338,237, to which reference should be made for further information. Additionally the reaction medium may comprise an added inert solvent, such as benzene, toluene, acetone, methyl iso-butyl ketone, t-butanol, n-butanol, tetralin, decalin, ethyl benzoate and the like. Usually, however, it will be preferred to operate in a "natural process solvent", i.e. a mixture of olefinically unsaturated compound, hydrogenation product(s) thereof, aldehyde product(s) and aldehyde condensation products. However, when operating continuously, it may be preferred to use at start up an inert solvent, such as acetone, benzene, toluene, or the like, and then gradually to allow this to be displaced by "natural process solvent" by differential evaporation as the reaction progresses.

The rhodium concentration in the liquid reaction medium may vary from about 10 ppm or less up to about 1000 ppm or more, calculated in each case as rhodium metal and on a weight/volume basis. Typically the rhodium concentration in the liquid reaction medium lies in the range of from about 40 ppm up to about 200 ppm, calculated as rhodium metal. For economic reasons it will not usually be desirable to exceed about 500 ppm rhodium, calculated as metal, in the liquid reaction medium.

In the liquid reaction medium the cyclic phosphite ligand:Rh molar ratio is desirably at least about 1:1. Preferably the ligand:Rh molar ratio is from about 3:1 or 4:1 up to about 20:1 or more. The upper limit of concentration of cyclic phosphite ligand in the reaction medium will usually be about 10% w/v or the solubility limit of the cyclic phosphite ligand therein, whichever is the lower figure. Usually, however, it will be preferred to operate at cyclic phosphite ligand concentrations of less than about 1% w/v and phosphite ligand:Rh molar ratios of from about 5:1 up to about 16:1, e.g. about 8:1. Good results can often be obtained at concentrations of 0.5% w/v or less, e.g. 0.25% w/v or less, of cyclic phosphite ligand.

At least some of the cyclic phosphite ligands used in the process of the invention are highly toxic; extreme care should therefore be taken in handling the phosphite ligands and reaction media containing them.

The reaction medium contains a stabilising amount of a tertiary amine. Thus there should be present in the reaction medium a small concentration of free tertiary amine sufficient to enhance the stability of the catalytic species by prevention of ligand degradation and to maintain catalyst activity. Whilst we do not wish to be bound by the correctness or otherwise of the following postulated mechanism, we believe that loss of catalyst activity after extended periods of operation is caused by degradation of the cyclic phosphite ligand, probably due to hydrolysis by water formed as a byproduct of aldolisation. Such hydrolytic reactions lead to ring opening of the cyclic phosphite and to production of acidic materials which then appear to catalyse the ring opening reaction, for example:

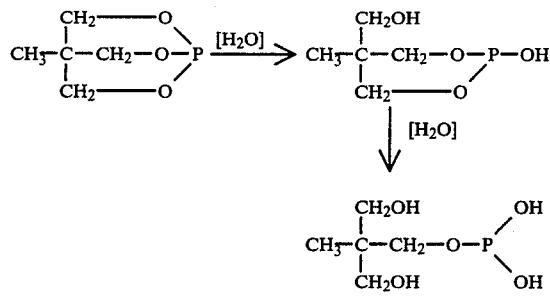

Hence the postulated ligand degradation is autocatalysing. The acidic ligand degradation products have three undesirable effects, the first being promotion of the formation of aldehyde condensation products, and the second effect being that the acidic ligand degradation products can protonate, or form a complex adduct with, the rhodium complex. This adduct is much less active as a hydroformylation catalyst. The third effect is the formation of less catalytically active rhodium species in the catalyst solution as the ligand concentration drops. This is shown as the colour of the solution progressively changes to yellow, orange, and then to red from the very pale original solution colour. An addition of fresh cyclic phosphite ligand to such a red-orange solution restores the colour to the original very pale state and increases the catalytic activity; the catalytic activity does not return to its original value unless an addition of a tertiary amine, such as a trialkylamine, is also made.

The function of the tertiary amine, we believe, is to react with and to neutralise the acidic hydrolysis products formed upon hydrolysis of the ligand and to release any rhodium bound to the acidic ligand degradation products thus restoring the activity of the catalyst solutions. The choice of a tertiary amine for this function is dictated by the desirability of using a basic material that is soluble in the reaction medium and does not tend to catalyse the formation of aldols and other aldehyde condensation products at a significant rate or to react with product aldehyde to give aldehyde/amine condensation products as would be the case if a primary or secondary amine was used.

The amount of tertiary amine present in the reaction medium is typically sufficient to provide a concentration of at least about 0.0001 moles of free amine per liter of reaction medium. Preferably the ratio of tertiary amine to total cyclic phosphite added (whether bound with rhodium or present as free phosphite) is at least about 0.1:1 and even more preferably at least about 0.5:1. Usually the tertiary amine:phosphite molar ratio will be at least about 1:1 up to about 5:1 or more. There is, however, normally little advantage in using a tertiary amine-phosphite ratio higher than about 5:1. Indeed the use of higher ratios may result in increased rates of formation of aldols and other aldehyde condensation products.

If a volatile tertiary amine, such as triethylamine or tri-n-propylamine, is used, this may be lost from the reaction medium during distillation for recovery of aldehyde product(s) as the amine will then tend to co-distil with the aldehyde product(s). In this case it will be necessary to add further tertiary amine, either continuously or in small aliquots from time to time, in order to maintain a stabilising amount of tertiary amine in the reaction medium. If a less volatile tertiary amine, such as tri-n-octylamine, is used then the rate of loss of amine upon recovery of product aldehyde(s) is correspondingly lower and no, or very infrequent, addition of further amine is required. Hence it is preferred to use a tertiary amine that has a boiling point significantly above that of the aldehyde product(s). For example, in hydroformylation of butene-1 according to the invention, it is preferred to use a relatively involatile tertiary amine such as tri-n-octylamine.

The hydroformylation conditions utilised in the process of the present invention involve use of elevated temperatures, e.g. in the range of from about 40° C. up to about 160° C. or more. Usually, however, it will be preferred to operate at as low a temperature as is possible, consistent with achieving a satisfactory reaction rate, so as to minimise the risk of isomerisation of the olefin (to a corresponding terminal olefin, in the case of an internal olefin, or to a corresponding internal olefin, in the case of an terminal olefin). Hence preferred operating temperatures usually range from about 70° C. up to about 130° C.; such temperatures are usually adequate both for alpha-olefins containing the group $-CH=CH_2$ and for internal olefins containing the group $-CH=CH-$. The reaction rate depends inter alia on the ligand:Rh molar ratio. Hence it will usually be necessary to increase the operating temperature, if the ligand:Rh molar ratio is increased beyond about 8:1, in order to maintain a substantially constant aldehyde productivity. When using ligand:Rh ratios of from about 3:1 to about 8:1, temperatures of about 70° C. to about 100° C. are usually suitable, both for alpha-olefins containing the group $-CH=CH_2$ and for internal olefins containing the group $-CH=CH-$; higher temperatures, e.g. up to about 130° C., may be desirable if higher ligand:Rh molar ratios, e.g. about 12:1 or more, are used. Higher temperatures may, however, be necessary where the olefinic carbon-carbon bond is more sterically hindered, as for example when the olefin contains the group >C=CH$_2$, —CH=CR— or —CR=CR—, where R is an organic radical (the free valencies indicated in the formulae for these radicals are in each case attached to an organic radical); for example, temperatures up to about 150° C. or higher may be necessary in this case in order to achieve satisfactory reaction rates. Use of such higher operating temperature will usually be accompanied by use of higher ligand:Rh molar ratios, e.g. about 8:1 or higher.

Elevated pressures are also typically used in the hydroformylation zone. Typically the hydroformylation reaction is conducted at a total pressure of from about 4 bar upwards up to about 75 bar or more. Usually it will be preferred to operate at a total pressure of not more than about 35 bar.

In the hydroformylation reaction 1 mole of carbon monoxide and 1 mole of hydrogen react with each olefinic bond. Thus, for example, in the case of butene-1, the major product is n-valeraldehyde which is formed by the reaction:

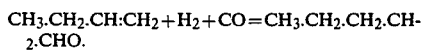

CH$_3$.CH$_2$.CH:CH$_2$+H$_2$+CO=CH$_3$.CH$_2$.CH$_2$.CH$_2$.CHO.

The isomeric aldehyde, 2-methylbutyraldehyde, is typically also fiormed as minor product as follows:

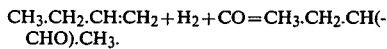

CH$_3$.CH$_2$.CH:CH$_2$+H$_2$+CO=CH$_3$.CH$_2$.CH(-CHO).CH$_3$.

In the case of an internal olefin, such as butene-2, the principal product is 2-methylbutyraldehyde which is formed by the reaction:

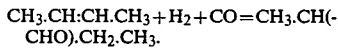

CH$_3$.CH:CH.CH$_3$+H$_2$+CO=CH$_3$.CH(-CHO).CH$_2$.CH$_3$.

A small amount of the isomeric aldehyde, n-valeraldehyde, typically less than 5% of the total aldehydes formed, may also be formed as follows:

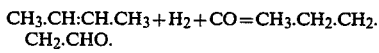

CH$_3$.CH:CH.CH$_3$+H$_2$+CO=CH$_3$.CH$_2$.CH$_2$.CH$_2$.CHO.

In addition some of the olefin may undergo hydrogenation; hence n-butane may be a byproduct when butene-1 or butene-2 is hydroformylated. Typically less than 5% of the olefin undergoes hydrogenation.

In operating the process of the invention in a continuous manner it is desirable to supply make up amounts of hydrogen and carbon monoxide in an approximately 1:1 molar ratio, e.g. about a 1.05:1 molar ratio. The formation of such mixtures of hydrogen and carbon monoxide can be effected by any of the methods known in the art for producing synthesis gas for hydroformylation, e.g. by partial oxidation of a suitable hydrocarbon feedstock such as natural gas, naphtha, fuel oil or coal.

In operating the process of the invention the total pressure of hydrogen and carbon monoxide in the hydroformylation zone can range from about 1.5 bar or less up to about 75 bar or more. The partial pressure of hydrogen may exceed that of carbon monoxide, or vice versa. For example the ratio of the partial pressure of hydrogen and of carbon monoxide may range from about 10:1 to about 1:10. At all events it will usually be desirable to operate at a partial pressure of hydrogen of at least about 0.05 bar up to about 30 bar and at a partial pressure of carbon monoxide of at least about 0.05 bar up to about 30 bar.

Product recovery can be effected in any convenient manner. In some instances, for example when using butene-1 or butene-2 as the olefinically unsaturated compound, it is possible to utilise a gas recycle process similar to that described in British Patent Specification No. 1582010. However, it may be more convenient to withdraw a portion of the liquid reaction medium from the hydroformylation zone either continuously or intermittently and to distil this in one or more stages under normal, reduced or elevated pressure, as appropriate, in a separate distillation zone in order to recover the aldehyde product(s) and other volatile materials in vaporous form, the rhodium-containing liquid residue being recycled to the hydroformylation zone. Condensation of the volatile materials and separation thereof, e.g. by distillation, can be carried out in conventional manner. Aldehyde product(s) can be passed on for further purification, whilst a stream containing unreacted olefin can be recycled to the hydroformylation zone together with any hydrogen and carbon monoxide that was dissolved in the reaction medium. A bleed stream can be taken from the recycle stream or streams in order to control build up of inerts (e.g. N$_2$) and of hydrogenation product(s) in the recycle streams.

The rhodium may be introduced into the reaction zone in any convenient manner. For example, the rhodium salt of an organic acid, such as rhodium acetate, i.e. [Rh(OCOCH$_3$)$_2$.H$_2$O]$_2$, can be combined with the ligand in the liquid phase and then treated with a mixture of carbon monoxide and hydrogen, prior to introduction of the olefin. Alternatively the catalyst can be prepared from a carbon monoxide complex of rhodium, such as dirhodium octacarbonyl, by heating with the cyclic phosphite ligand which thereby replaces one or more of the carbon monoxide molecules. It is also possible to start with the ligand of choice and finely divided rhodium metal, or with an oxide of rhodium (e.g. Rh$_2$O$_3$ or Rh$_2$O$_3$.H$_2$O) and the ligand, or with a rhodium salt of an inorganic acid, such as rhodium nitrate (i.e. Rh(NO$_3$)$_3$.2H$_2$O) and the ligand, and to prepare the active species in situ during the course of the hydroformylation reaction. Yet again it is possible to introduce into the reaction zone, as a catalyst precursor, a rhodium complex such as (pentane-2,4-dionato)dicarbonyl rhodium (I) which is then converted, under the hydroformylation conditions and in the presence of excess ligand, to the operative species. Other suitable catalyst precursors include Rh$_4$(CO)$_{12}$ and Rh$_6$(CO)$_{16}$.

When using polymeric aldehyde condensation products as solvent, the ratio of aldehyde to such products in the liquid reaction mixture in the hydroformylation zone may vary within wide limits. Typically this ratio lies in the range of from about 1:5 to about 5:1 by weight.

Under appropriate conditions aldehyde productivities in excess of about 0.5 g. moles/liter of catalyst solution/hr can be achieved in the process of the invention. Hence it is usually preferred to supply make up olefin to the hydroformylation zone at a rate which at least corresponds to the aldehyde productivity of the system under the hydroformylation conditions selected. As the conversion per pass will usually be less than 100%, typically about 15% to about 80% or higher, it will be necessary to increase correspondingly the feed rate of the make up olefin if the process is to operate on a "once through" basis or to recycle unreacted olefin at an appropriate rate if the process operates with olefin recycle. Often the aldehyde productivity rate exceeds about 1.0 g. mole/liter/hr, e.g. up to at least about 1.5 g. moles/liter/hr and the rate of supply of make up olefin must then equal or exceed this value.

The ligand stabilising effect of the tertiary amine appears from the results of our experiments to be shown only with cyclic phosphite ligands, such as 4-ethyl-2,6,7-trioxaphosphabicyclo-[2,2,2]-octane, and not with "open" (or acyclic) phosphites, such as triphenylphosphite.

The invention is illustrated further in the following Examples. In these Examples the conditions have been selected with a view to accelerating decay of the ligand so that the experiments could be completed within a reasonable time and are not necessarily the conditions that would be selected for operation of a commercial plant.

EXAMPLE 1

The continuous hydroformylation of butene-1 was investigated using a stainless steel reactor of nominal capacity 300 ml which is fitted with a magnetically coupled stirrer and with an internal cooling coil through which air could be blown for temperature control purposes. The reactor was also fitted with a gas inlet tube for admission of a $CO/H_2$ mixture to the gas space and an inlet tube for liquid butene-1, each in the form of a dip tube ending near the bottom of the reactor, as well as with a liquid outlet tube in the form of a dip tube whose open lower end was positioned at a level corresponding to the surface level of a volume of 150 ml of liquid in the reactor. Butene-1 was charged to a feed vessel which was pressurised to 4.5 kg/cm$^2$ absolute (446 kPa) with $O_2$-free nitrogen and which was connected to the corresponding inlet tube of the reactor by way of a feed pump and a non-return valve. Carbon monoxide and hydrogen were supplied from individual cylinders thereof through individual pressure controllers and then by way of a two channel mass flow controller through an oxygen guard unit (to ensure that the synthesis gas fed to the reactor was oxygen-free).

Liquid in excess of 150 ml together with unreacted gases exited the reactor through the outlet tube and passed through a cooler to a gas-liquid separator which acted as a knock out pot. The gas from the knock out pot was passed through a letdown valve which let its pressure down to atmospheric pressure and was then supplied to a wet gas meter and vented. The separated reactor solution in the knock out pot was maintained at a specific volume using a level controller which let down excess liquid through a capillary tube to a product evaporator consisting of a Liebig condenser packed with glass beads. The majority of the liquid passed through the beads and fell into a receiver which was also fitted with a level controller. When this level controller indicated that the liquid in the receiver exceeded a preselected volume hot oil was pumped through the evaporator. The stripped reactor solution was pumped back from the receiver to the reactor at a constant rate by means of a catalyst recycle pump.

The flashed butene-1 and product passed overhead through a cooler to the product receiver, where the majority of the product was collected. Some of the unreacted butene-1 was dissolved in the product condensate, whilst the remainder passed on through a meter.

The reactor was heated by immersion in a thermostatically controlled oil bath, fine temperature control being exerted automatically by blowing air on demand through the internal cooling coil. The level controllers were set so that the total liquid inventory of the catalyst containing solution was 200 ml, i.e. an inventory of 50 ml outside the reactor.

To monitor the course of the reaction the gas flow rates were measured and gas chromatographic analyses were performed by sampling the system as follows:

| Sample stream | Components |
| --- | --- |
| Inlet synthesis gas | $H_2$, CO |
| Exit gas from knock out pot | $H_2$, CO, aldehydes, butenes, butane |
| Butene off gas | $H_2$, CO, butenes, butane, aldehydes |
| Product | Aldehydes, aldehyde byproducts, butenes, butane |
| Reactor solution | Aldehydes, aldehyde byproducts, butenes, butane, ligand concentration |

$H_2$ and CO were determined using a 1.85 m×4.76 mm o.d. stainless steel column packed with molecular sieve (5 Å) at 110° C. Butenes and butane were determined using a 1.85 m×4.76 mm o.d. stainless steel column packed with Porasil C at 60° C. Aldehydes and aldehyde byproducts were determined using a 1.85 m×4.76 mm o.d. stainless steel column packed with 10% OV 101 on Chromosorb PAW which was temperature programmed to run at 50° C. for 5 minutes and then to increase in temperature at 10° C./minute to 300° C. Ligand concentration was determined using a phosphorus specific flame photometric detector and a 0.46 m×4.76 mm o.d. stainless steel column packed with 10% OV 101 on Chromosorb PAW run at 220° C. ("Porasil" and "Chromosorb" are trade marks).

At start up the empty reactor was purged with nitrogen and then pressurised to 21.7 bar with the $CO/H_2$ mixture and a flow of the hydrogen/carbon monoxide mixture in excess of the anticipated reaction demand was established through the system using the mass flow controllers. Then acetone was charged to the system via the sample point for the product evaporator bottoms using the catalyst recycle pump. When 100 ml of acetone had been charged the reactor stirrer was switched on and adjusted to run at 1500 r.p.m. Once automatic level control had been achieved addition of acetone was terminated. The feedstock pump was then switched on so as to give a butene-1 feed rate of 68 ml/hr and the system allowed to equilibrate under automatic control.

Next 0.1 g [Rh(OCOCH$_3$)$_2$.H$_2$O]$_2$ (equivalent to 0.418 millimoles of Rh) and 0.5 g (3.08 millimoles) TMPP, i.e. 4-ethyl-2,6,7-trioxa-1-phosphabicyclo-[2,2,2]-octane, were charged to the system via the evaporator bottoms sample point. This corresponds to a TMPP:Rh molar ratio of 7.4:1. When the system was homogeneous the reactor temperature was raised to 77° C. Onset of reaction was detected by a decrease in the effluent synthesis gas from the knock out pot, accompanied by more frequent operation of the oil pump to the product evaporator and by the appearance of liquid in the product receiver. As the reaction proceeded the acetone initially charged to the system was replaced within the system by product aldehydes.

The various data measured are set out in Table I below. The catalyst solution recycle rate was 64.5 ml/hr. The H$_2$:CO ratio was 1:1.

this was not maintained, the loss in catalyst activity being ascribed to loss of the volatile triethylamine due to carry-over with product aldehydes.

TABLE I

| Duration (Hrs) | Temp. (°C.) | Butene-1 Feed Rate (Cm$^3$/hr) | Reaction Rate (g mol/l/hr) | Butene-1 Conversion (%) | Activity Index | TMPP Conc. (% w/v) | Tert. Amine Conc. (% v/v) | Selectivity (Excluding Hydrogenation) 2-MBAL | VAL | ISOM |
|---|---|---|---|---|---|---|---|---|---|---|
| 6 | 77.3 | 68.0 | 3.45 | 71.1 | 236 | | 0 | 30.2 | 69.0 | 0.5 |
| 24 | 77.6 | 68.0 | 3.65 | 73.4 | | | 0 | | | |
| 36 | 77.2 | 68.0 | 3.50 | 71.1 | 238 | | 0 | 30.2 | 69.0 | 0.5 |
| 60 | 77.4 | 71.1 | 3.52 | 71.1 | 239 | 0.13 | 0 | | | |
| 168 | 77.2 | | | | | 0.07 | 0 | | | |
| 174 | 77.2 | 70.3 | 3.52 | 71.2 | 249 | 0.04 | 0 | 30.8 | 65.6 | 3.6 |
| 182 | 72.9 | | | | | 0.04 | 0 | | | |
| 185 | 72.8 | 70.5 | 2.64 | 54.6 | 117 | | 0 | 28.8 | 65.0 | 6.2 |
| 189 | 69.0 | | | | | 0.05 | 0 | | | |
| 192 | 68.9 | | | | | 0.04 | 0 | | | |
| 195 | 68.9 | 70.2 | 1.93 | 40.1 | 64 | | 0 | 28.0 | 66.0 | 6.0 |
| 203 | 77.3 | 72.6 | 3.46 | 67.7 | 150 | 0.17 | 0 | 29.1 | 67.3 | 3.6 |
| 209 | 76.9 | 70.3 | 2.83 | 57.5 | 135 | 0.18 | 0 | 27.8 | 68.6 | 3.6 |
| 227 | 77.2 | | | | | 0.11 | 0 | | | |
| 232 | 77.3 | 69.1 | 3.05 | 61.5 | 161 | | 0 | 29.1 | 69.7 | 1.2 |
| 235 | 77.2 | | | | | 0.15 | 0 | | | |

ISOM = cis- and trans-butene-2
2-MBAL = 2-methylbutyraldehyde
VAL = n-valeraldehyde.

The term "Activity Index" in Table I is defined as:

Throughout this Example there was less than 2% hydrogenation observed to n-butane.

TABLE II

| Duration (Hrs) | Temp. (°C.) | Butene-1 Feed Rate (Cm$^3$/hr) | Reaction Rate (g mol/l/hr) | Butene-1 Conversion (%) | Activity Index | TMPP Conc. (% w/v) | Et$_3$N Conc. (% v/v) | Selectivity (Excluding Hydrogenation) 2-MBAL | VAL | ISOM |
|---|---|---|---|---|---|---|---|---|---|---|
| 236 | | | | | | | 0.10 | | | |
| 237 | 77.2 | | | | 260 | 0.14 | 0.01 | | | |
| 242 | 77.4 | | | | 230 | 0.13 | 0.01 | | | |
| 244 | 77.4 | 65.7 | 3.23 | 68.6 | 216 | | | 29.8 | 69.0 | 1.2 |
| 249 | 77.5 | | | | 165 | 0.10 | 0.01 | | | |
| 251 | 77.4 | 64.1 | 3.01 | 65.2 | 183 | 0.09 | | 30.0 | 68.7 | 1.3 |
| 256 | 77.5 | | | | 171 | 0.11 | | | | |

$$\text{Activity index} = \frac{\text{productivity (gmol/l/hr)}}{\text{reactor olefin concentration (\% v/v)}} \times 1000$$

It will be seen from Table I that the TMPP declined from its initial level of 0.25% w/v to 0.13% w/v after 60 hours and to 0.04% w/v after 192 hours. Accordingly a further 0.3 g TMPP was introduced into the reactor after 196 hours. A decline in Activity Index from a value of 249 after 174 hours to a value of 161 after 232 hours was recorded.

After 235 hours 0.86 ml triethylamine was introduced into the reactor; the results are shown in Table II. The concentration of amine was that measured in the recycle solution. A marked increase in activity was noted, the Activity Index being 260 after 236 hours. However

EXAMPLE 2

The run of Example 1 was continued, 0.55 ml tri-n-propylamine being added after 256 hours from the commencement of the run. The results are listed in Table III. Again a marked increase in Activity Index was noted and the rate of loss of catalyst activity was considerably less than when triethylamine was added. A further 0.55 ml aliquot of tri-n-propylamine was introduced into the reactor after 280 hours. Again the Activity Index increased and was better maintained than with triethylamine. Throughout this Example the extent of hydrogenation to n-butane was less than 2%.

TABLE III

| Duration (Hrs) | Temp. (% C.) | Butene-1 Feed Rate (Cm$^3$/hr) | Reaction Rate (g mol/l/hr) | Butene-1 Conversion (%) | Activity Index | TMPP Conc. (% w/v) | (n-Pr)$_3$N Conc. (% v/v) | Selectivity (Excluding Hydrogenation) 2-MBAL | VAL | ISOM |
|---|---|---|---|---|---|---|---|---|---|---|
| 262 | 77.5 | | | | 260 | 0.08 | 0.13 | | | |
| 273 | 77.2 | | | | 235 | 0.13 | 0.01 | | | |
| 275 | 77.2 | 65.7 | 3.37 | 71.4 | 247 | | | 29.9 | 69.0 | 1.1 |
| 276 | 77.1 | | | | 253 | 0.13 | 0.01 | | | |
| 284 | 77.6 | | | | 290 | 0.19 | 0.24 | | | |
| 290 | 77.4 | | | | 310 | | 0.14 | | | |
| 293 | 77.5 | 65.3 | 3.52 | 75.1 | 299 | | | | | |
| 293 | 77.6 | | | | 280 | 0.17 | 0.03 | 29.9 | 68.8 | 1.3 |
| 300 | 77.5 | | | | 301 | 0.17 | 0.01 | | | |

EXAMPLE 3

A similar run was carried out to investigate the use of tri-n-octylamine as stabilising tertiary amine, using the same general procedure as described in Example 1, under the following conditions:

| | |
|---|---|
| Rhodium concentration | 200 ppm w/v (calculated as rhodium metal) |
| Temperature | 101° C. |
| Butene-1 feed rate | 60 ml/hr |
| Recycle rate | 60 ml/hr |
| Pressure | 21.7 bar |
| H$_2$:CO molar ratio | 0.25% w/v |
| Total solution volume | 200 ml |

Initially no tri-n-octylamine was charged to the reactor. The results are listed in Table IV. The ligand was observed to be stable for the first 30 hours of operation. 1 ml water was added after 30 hours and again after 46 hours. This promoted ligand decay. After 51 hours 0.5 g TMPP and 1 ml tri-n-octylamine were added. Over the next 24 hours the ligand appeared to be quite stable. After 75 hours the ligand concentration was raised by adding a further 0.5 g TMPP and an additional 1.3 ml tri-n-octylamine was added. Excellent ligand stability was observed at the higher ligand:rhodium molar ratio and higher ligand concentration. After 105 hours 1.0 ml triphenylphosphite and a further 1.3 ml tri-n-octylamine was added. Although the concentration of TMPP remained steady, it was noted that triphenylphosphite decayed rapidly. A further addition of triphenylphosphite was made after 115 hours but again it degraded rapidly although the TMPP did not decay significantly.

triethanolamine, a beneficial ligand stabilising effect is observed.

What is claimed is:

1. A continuous hydroformylation process for the production of an aldehyde selected from the group consisting of linear aldehydes and non-liner aldehydes by hydroformylation of an olefin selected from the group consisting of alpha-olefins, substituted alpha-olefins, internal olefins and substituted internal olefins, which comprises:

providing a hydroformylation zone containing a charge of a liquid reaction medium having dissolved therein (a) a complex rhodium hydroformylation catalyst comprising rhodium in complex combination with carbon monoxide and with a cyclic phosphite having a phosphorus atom linked to three oxygen atoms at least two of which form together with the phosphorus atom part of a ring and (b) a ligand stabilising amount of tertiary amine;

supplying said olefin to the hydroformylation zone;

maintaining in the hydroformylation zone a temperature in the range of from about 40° C. to about 160° C. and a pressure in the range of from about 4 bar to about 75 bar; supplying make-up hydrogen and carbon monoxide to the hydroformylation zone; and recovering from the liquid hydroformylation medium a hydroformylation product comprising at least one aldehyde selected from the group consisting of linear aldehydes and non-linear aldehydes.

2. A process according to claim 1, in which the cyclic phosphite is a bicyclic phosphite of the general formula:

TABLE IV

| Run Time (Hours) | 2 | 4 | 6 | 8 | 10 | 12 | 14 | 16 | 18 | 20 | 22 | 24 |
|---|---|---|---|---|---|---|---|---|---|---|---|---|
| Free Ligand Conc in Recycle Soln (% w/v) | 0.20 | 0.16 | 0.15 | 0.15 | 0.15 | 0.15 | 0.16 | 0.14 | 0.16 | 0.14 | 0.16 | 0.15 |
| Trioctylamine Conc in Recycle Soln (% w/v) | — | — | — | — | — | — | — | — | — | — | — | — |
| Run Time (Hours) | 28 | 28 | 30 | 32 | 34 | 36 | 38 | 40 | 42 | 44 | 46 | 48 |
| Free Ligand Conc in Recycle Soln (% w/v) | 0.15 | 0.14 | C* | 0.13 | 0.11 | 0.10 | 0.10 | 0.10 | 0.10 | 0.09 | C* | 0.07 |
| Trioctylamine Conc in Recycle Soln (% w/v) | — | — | — | — | — | — | — | — | — | — | — | — |
| Run Time (Hours) | 50 | 51 | 52 | 54 | 56 | 58 | 60 | 62 | 64 | 66 | 68 | 70 |
| Free Ligand Conc in Recycle Soln (% w/v) | 0.05 | A* | 0.33 | 0.34 | 0.36 | 0.33 | 0.32 | 0.31 | 0.31 | 0.31 | 0.32 | 0.30 |
| Trioctylamine Conc in Recycle Soln (% w/v) | — | D* | 2.74 | 2.78 | 2.77 | 2.85 | 2.96 | 2.88 | 2.89 | 2.61 | 2.83 | 2.77 |
| Run Time (Hours) | 72 | 74 | 75 | 76 | 78 | 80 | 82 | 84 | 86 | 88 | 90 | 92 |
| Free Ligand Conc in Recycle Soln (% w/v) | 0.29 | 0.29 | A* | 0.68 | 0.66 | 0.63 | 0.64 | 0.62 | 0.63 | 0.62 | 0.63 | 0.61 |
| Trioctylamine Conc in Recycle Soln (% w/v) | 2.59 | 2.61 | D* | 4.17 | 4.54 | 4.65 | 4.48 | 4.73 | 4.63 | 4.64 | 4.60 | 4.06 |
| Run Time (Hours) | 94 | 96 | 98 | 100 | 102 | 104 | 105 | | | | | |
| Free Ligand Conc in Recycle Soln (% w/v) | 0.60 | 0.61 | 0.58 | 0.57 | 0.56 | 0.55 | D* | | | | | |
| Trioctylamine Conc in Recycle Soln (% w/v) | 4.22 | 4.40 | 4.25 | 4.20 | 4.06 | 3.87 | E* | | | | | |
| Run Time (Hours) | 106 | 108 | 110 | 112 | 114 | 115 | 116 | 118 | 120 | 122 | 125 | |
| Free Ligand Conc in Recycle Soln (% w/v) | 0.56 | 0.58 | 0.58 | 0.59 | 0.58 | | 0.58 | 0.57 | 0.55 | 0.56 | A* | |
| Trioctylamine Conc in Recycle Soln (% w/v) | 5.65 | 5.91 | 6.02 | 5.84 | 6.19 | | 5.89 | 5.81 | 5.83 | 5.88 | D* | |
| Triphenyl phosphite Conc in Recycle Soln (% w/v) | 0.50 | 0.33 | 0.10 | 0.03 | 0.01 | E* | 0.60 | 0.37 | 0.14 | 0.04 | | |

A* Ligand Added
C* Water Added
D* Trioctylamine Added
E* Triphenylphosphite Added

EXAMPLE 4

Similar experiments to those described in Examples 1 to 3 are carried out using the olefins butene-2, allyl t-butyl ether, dodecene-1 and n-propyl oct-7-enoate under appropriate hydroformylation conditions. Using the compounds TMPP, 4-acetoxymethyl-2,6,7-trioxa-1-phosphabicyclo-[2,2,2]-octane, 4-n-hexyl-2,6,7-trioxa-1-phosphabicyclo-[2,2,2]-octane, 4-methyl-2,6,7-trioxa-1-phosphabicyclo-[2,2,2]-octane, and 2,8,9-trioxa-1-phosphatricyclo-[3.3.1.1$^{3,7}$]-decane as well as the amines N,N-diethylaniline, pyridine, N-methylmorpholine, and

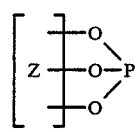

(I)

in which Z represents a trivalent acyclic organic group.

3. A process according to claim 2, in which the cyclic phosphite ligand is selected from 4-methyl-2,6,7-trioxa-1-phosphabicyclo-[2,2,2]-octane, 4-ethyl-2,6,7-trioxa-1- phosphabicyclo-[2,2,2]-octane, 4-ethoxymethyl-2-6,7-trioxa-1-phosphabicyclo-[2,2,2]-octane, and 4-acetoxymethyl-2,6,7-trioxa-1-phosphabicyclo-[2,2,2]-octane.

4. A process according to claim 1, in which the cyclic phosphite ligand is a monocyclic phosphite of the general formula:

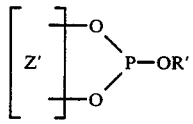

(VI)

in which Z' represents a divalent cyclic or acyclic organic radical and R' represents an optionally substituted alkyl or aryl radical.

5. A process according to claim 1, in which the tertiary amine is a trialkylamine.

6. A process according to claim 5, in which the tertiary amine is selected from triethylamine, tri-n-propylamine and tri-n-octylamine.

7. A process according to claim 1, in which the olefin is butene-1 and the hydroformylation product comprises n-valeraldehyde.

8. A process according to claim 1, in which the olefin is butene-2 and the hydroformylation product comprises 2-methylbutyraldehyde.

9. A process according to claim 1, in which the hydroformylation zone is maintained at a temperature of from about 40° C. up to about 160° C., at a total pressure of from about 4 bar up to about 35 bar, at a partial pressure of hydrogen and of carbon monoxide each of at least about 0.05 bar, and at a ratio of partial pressures of hydrogen and of carbon monoxide in the range of from about 10:1 to about 1:10.

10. A process according to claim 1, in which the cyclic phosphite ligand:Rh molar ratio is at least about 3:1.

11. A process according to claim 1, in which recovery of the hydroformylation product includes withdrawal of reaction medium from the hydroformylation zone and distillation thereof in one or more stages under normal, reduced or elevated pressure.

12. A process according to claim 11, in which the distillation step yields also a stream comprising unreacted olefin which is recycled to the hydroformylation zone.

13. A process according to claim 1, in which the reaction medium comprises aldehyde product and aldehyde condensation products as solvent.

14. A process according to claim 1, in which make-up olefin is supplied to the hydroformylation zone at a rate corresponding to at least about 0.5 gram moles per liter of reaction medium per hour.

15. A process according to claim 1, in which the cyclic phosphite is formed in situ by transesterification of an organic phosphite of the general formula:

(R'O)₃P  (IV)

in which each R' is an optionally substituted alkyl or aryl radical with a triol or higher polyol of the general formula:

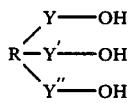

(V)

in which Y, Y' and Y" each, independently of the others, represent a divalent organic radical, and R is a trivalent atom or group, or with a diol of the general formula:

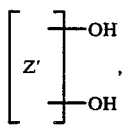

(VIII)

in which Z' represents a divalent organic radical.

16. A process according to claim 1, in which the cyclic phosphite is a tricyclic or polycyclic phosphite of the general formula:

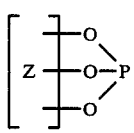

(I)

in which Z comprises a cyclic organic group.

17. In a continuous hydroformylation process for the production of an aldehyde by hydroformylation of an olefin which comprises:
providing a hydroformylation zone containing a charge of a liquid reaction medium having dissolved therein a complex rhodium hydroformylation catalyst comprising rhodium in complex combination with carbon monoxide and with a cyclic phosphite having a phosphorus atom linked to three oxygen atoms at least two of which form together with the phosphorus atom part of a ring;
supplying said olefin to the hydroformylation zone;
maintaining in the hydroformylation zone a temperature in the range of from about 40° C. to about 160° C. and a pressure in the range of from about 4 bar to about 75 bar;
supplying make-up hydrogen and carbon monoxide to the hydroformylation zone; and
recovering from the liquid hydroformylation medium a hydroformylation product comprising at least one aldehyde selected from the group consisting of linear aldehydes and non-linear aldehydes,
the improvement comprising providing in the liquid reaction medium a ligand stabilising amount of tertiary amine dissolved therein thereby to increase the stability of the cyclic phosphite ligand in the liquid reaction medium under the hydroformylation conditions used.

* * * * *